Figure 1:
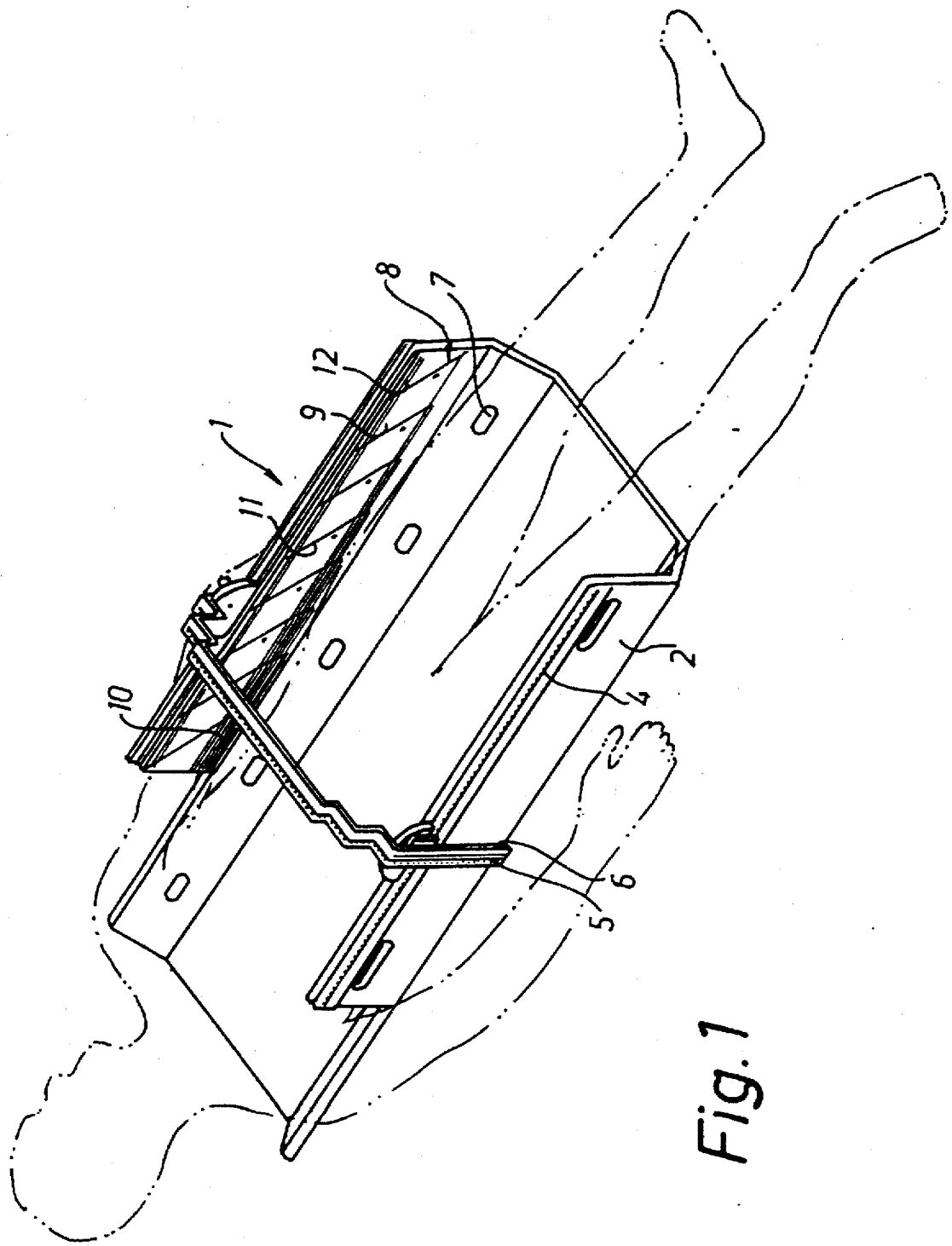

United States Patent [19]
Lax

[11] Patent Number: 5,681,326
[45] Date of Patent: Oct. 28, 1997

[54] STEREOTACTICAL INSTRUMENT

[75] Inventor: Ingemar Lax, Stockholm, Sweden

[73] Assignee: Elekta Instrument AB, Stockholm, Sweden

[21] Appl. No.: 537,938

[22] PCT Filed: Jun. 13, 1994

[86] PCT No.: PCT/SE94/00574

§ 371 Date: Nov. 3, 1995

§ 102(e) Date: Nov. 3, 1995

[87] PCT Pub. No.: WO94/28817

PCT Pub. Date: Dec. 22, 1994

[30]    Foreign Application Priority Data

Jun. 15, 1993 [SE] Sweden ................................. 9302066

[51] Int. Cl.$^6$ .................................................. A61B 19/00
[52] U.S. Cl. ........................ 606/130; 128/653.1; 378/163
[58] Field of Search ............................. 606/130; 604/119; 128/653.1; 378/162, 163, 164, 205, 209

[56]            References Cited

U.S. PATENT DOCUMENTS

| 4,622,185 | 11/1986 | Kostich ................................. | 264/45.2 |
| 4,905,267 | 2/1990 | Miller et al. ........................... | 378/208 |
| 5,147,372 | 9/1992 | Nymark et al. . | |
| 5,242,455 | 9/1993 | Skeens et al. ........................ | 606/130 |
| 5,281,232 | 1/1994 | Hamilton et al. .................... | 606/130 |
| 5,299,253 | 3/1994 | Wessels ................................. | 378/163 |

FOREIGN PATENT DOCUMENTS 2 377 795   8/1978   France .

OTHER PUBLICATIONS

Abstract and drawings from Swedish patent application 8802620-8 filed in 1988 (with English translation).

"Biopsibage Minimerar Felstik," *Medicinsk Teknik*, No. 3, 1990, pp. 23-24.

*Primary Examiner*—Robert A. Hafer
*Assistant Examiner*—Benjamin Koo
*Attorney, Agent, or Firm*—Shapiro and Shapiro

[57]            ABSTRACT

A stereotactical instrument for identifying a spatial position of an area in a patient's body which is to be subjected to treatment, preferably radiation treatment, the position of the area being previously determined, for example, by an angiogram, PET, DSA, CT, MRI, or X-ray equipment. The instrument includes a non-yielding and radiolucent frame which is arranged to support the patient's body and to support an indicating device, a radiolucent fixing device which is arranged inside the frame and on which the patient's body is intended to rest, the fixing device including a flexible casing which contains a yieldable substance, at a first stage the fixing device being adapted to permit that the patient is oriented in a desired position, partly sunk into the fixing device, and at a second stage the yieldable substance of the fixing device being given a non-yielding state, thereby fixing the patient in the desired position, and a partially non-radiolucent orienting device which is mounted on at least one longitudinal side of the frame and which is adapted to indicate the position of an image sectional plane through the area in the patient's body.

12 Claims, 2 Drawing Sheets

STEREOTACTICAL INSTRUMENT

The present invention relates to a stereotactical instrument for identifying, by means of image sectional planes or markers, the spatial position of an area in a patient's body which is to be subjected to treatment, preferably radiation treatment, the position of the area being previously determined, for example by means of angiogram, PET, DSA, CT, MRI or X-ray equipment. The instrument comprises a non-yielding and radiolucent frame which is arranged to support the patient's body and to support an indicating device, a radiolucent fixing means which is arranged inside the frame and on which the patient's body is intended to rest. The fixing means comprises a flexible casing which contains a yieldable substance, at a first stage the fixing means being adapted to permit that the patient be oriented in a desired position, partly sunk into the fixing means, and at a second stage the yieldable substance of the fixing means being given a non-yielding state, thereby fixing the patient in the desired position.

In radiation treatment as well as in surgical operations, the ability to identify the target area with great accuracy is highly important. To minimise the risk, the surgeon must be sure of hitting the correct area in the treatment.

It is vital that the treatment area can be easily and safely identified on different occasions, since, for example, fractionated radiation treatment requires a number of successive treatment sessions.

U.S. Pat. No. 5,147,372 discloses a computerised tomography unit which comprises a radiation-damping and perforated biopsy arch which is displaceably and pivotally attached to the treatment table on which the patient is placed. By means of the X-ray radiation in CT equipment, a sectional image is obtained in which the biopsy arch is outlined, a suitable hole in the biopsy arch being selectable for introducing a needle point in the target area. Although this prior art unit permits in a simple way the target area to be found, the accuracy is jeopardised by the patient not being fixed to the treatment table. Besides, the unit is not intended for radiation treatment.

The object of the present invention is to provide a stereotactical instrument with high accuracy when identifying the target area.

A further object of the invention is to provide a stereotactical instrument which permits safe and repeatable identification of the treatment area.

According to the invention, these objects are achieved by means of an instrument as described above, which is characterised by a partially non-radiolucent orienting means which is mounted on at least one longitudinal side of the frame and which is adapted to indicate the position of the respective image sectional plane through said area in the patient's body, and by the orienting means comprising a first array of lines of different lengths.

Further developments of the invention are describe below.

Figure 2:
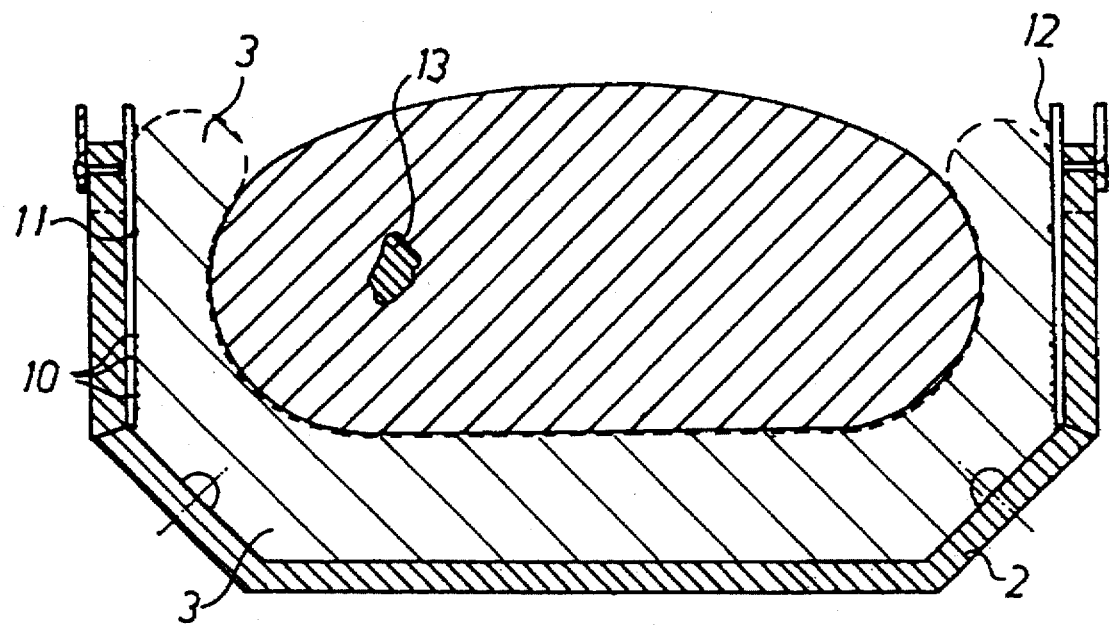

A preferred embodiment of the invention will now be described for the purpose of exemplification, reference being made to the accompanying drawings in which:

FIG. 1 is a perspective schematic view of a patient testing in the frame of an embodiment of the instrument; and FIG. 2 illustrates an image sectional plane and its orientation the stereotactical system of coordinates.

The inventive stereotactical instrument, which generally designated 1 in FIG. 1, comprises an elongate, non-yielding frame 2 which is made of a material that does not cause any artifacts (disturbances) in the images, i.e., a material which is translucent to X-rays and other radioactive radiation. A fixing means 3 is adapted to be inserted in the frame 2 which is open at the top and at the ends, said fixing means comprising a flexible casing which is impermeable to fluid and hermetically encloses a yielding substance, not shown in FIG. 2. On this fixing means, the patient is caused to take the desired position for diagnostics or treatment, the patient partially sinking into the yieldable fixing means, and a large contact surface against the patient is obtained, see FIG. 2. Subsequently, the fixing means 3 is given a non-yielding state so as to fix the patient in the desired position. This can be achieved by the casing of the fixing means holding a plurality of small bodies, for example so-called Frigolit beads or the like, which are fixed in their respective positions when a negative pressure is produced in the impermeable casing. It is also possible to fill the casing with a fluid which can be caused to solidify so as to keep its enforced shape. Thus, the casing can be filled with prepolymerised polyurethane foam which, when the patient has been oriented in the desired position, is caused to finally polymerise and thus form a non-yielding, fixing compound. By means of a first indicating device 4 fixedly arranged on the frame 2 in the longitudinal direction thereof, and a second indicating device 5 arranged on an arch 6 which is displaceable on the frame in the longitudinal direction thereof, the patient can be oriented in the fixing means for treatment of an area which has previously been located by means of computerised tomography, X-rays etc.

The frame 2 is preferably formed with fixing holes (not shown) into which the fixing means can penetrate a; its first, yielding stage, and/or fixing lugs 7 penetrating into the fixing means so as to fix this at its second, non-yielding stage.

Finally, the frame 2 comprises one or more orienting means 8 along each longitudinal side of the frame. The orienting means 8 which preferably is releasably attached to the inside of the frame, consists of a radiolucent support with three arrays of lines preventing radiation, which are made of, e.g., wire, strips or thin sections of copper for diagnostic X-ray, angiography, DSA and CT examinations or gas-, liquid- or substance-filled tubes for diagnostic PET and MRI examinations. The first array 10 comprises a number of lines of different lengths extending in parallel from one open end of the frame, said lines preferably being parallel also with the bottom of the frame, as shown in FIG. 1. The second array 11 comprises parallel lines extending at an angle to the first array 10 and extending from the first array along each longitudinal side of the frame. The second array 11 is terminated at a third array 12 adjacent the upper edge of the longitudinal side. The third array 12 comprises one or more unbroken lines which preferably are parallel with the lines of the first array. See also FIG. 2 which schematically illustrates a vertical section of the orienting means 8. In this Figure, the frame 2 is indicated by full lines and the upper surface of the fixing means 3 by dashed lines.

The frame 2 is supported by a bed unit which allows the patient to be moved, fixed in the frame.

The diagnostic equipment produces an image section, for example an MRI or CT sectional image, and the orientation of this section is indicated by the orienting means 8. By counting the number of lines in the first array 10, a base value is obtained. The distance between the uppermost unbroken line in the first array and the point in which the image section cuts one of the inclined lines in the second array is measured and yields a supplementary value, see FIG. 2. Since the distance between the two upper horizontal marks 11 and 12 is known, this distance can be used as a reference for calculating the vertical coordinate in the image sectional plane. Similarly, the horizontal coordinate in the image plane can be calculated by the distance between 11 and 12 on the two sides of the frame being known. By means of these values, the orientation of the image section can be determined with great accuracy. It should be noted that the image section need not be oriented at right angles to the longitudinal axis of the frame 2, but may be oriented at an optional angle, as shown in FIG. 2 in which each point of intersection between The image section and the associated line in The second array 11 is positioned on different levels. This Figure schematically illustrates a sectional image of the patient in which the target area or treatment area 13 appears. In diagnostic use, the orienting accuracy of the stereotactical system has been about 1 mm, and in repeated treatment using the stereotactical instrument the orienting accuracy has been about 3 mm in the transverse plane and about 6 mm in the longitudinal plane. These values were obtained for target areas close to the diaphragm and were to a certain extent affected by the patient's breathing. In order to reduce the effect of the breathing movements, an abdomen belt (not shown) may be used on such occasions.

The stereotactical coordinates are adjusted on the scales 4 and 5 in the treatment room by means of prior-art wall-mounted lasers, mounted-and set in conventional manner, which define the system of coordinates for the room/treatment unit. Guided by the values which are obtained in the locating of the target point, i.e. the tissue area To be treated, and which are transferred to the stereotactical instrument, the coordinates are obtained which are necessary to be able to set a radiation source, starting from the frame, such that the beam therefrom is directed to the treatment site or target point.

The invention is not restricted to that described above and illustrated in the drawings, but may be modified within the scope of the claims.

I claim:

1. A stereotactical instrument for identifying a spatial position of an area in a patient's body which is to be subjected to treatment, the spatial position of the area having been previously determined, the instrument comprising:

a non-yielding and radiolucent frame which is arranged to support the patient's body;

a radiolucent fixing means which is arranged inside the frame and on which the patient's body is intended to rest, said fixing means comprising a flexible casing which contains a yieldable substance, the fixing means being adapted to permit the patient to be partly sunk into the fixing means and oriented in a desired position at a first stage, and the yieldable substance of the fixing means being transformable into a non-yielding state to fix the patient in the desired position at a second stage; and a partially non-radiolucent orienting means which is mounted on at least one longitudinal side of the frame and which is adapted to indicate the position of an image sectional plane through said area in the patient's body, the orienting means comprising a first array of parallel lines of different lengths and a second array of parallel lines extending at an acute angle to the first array of parallel lines, all of said lines blocking radiation.

2. A stereotactical instrument as claimed in claim 1, wherein the frame comprises at least one of fixing holes and fixing lugs for preventing relative movement between the frame and the fixing means when in the second stage.

3. A stereotactical instrument as claimed in claim 1, wherein the orienting means comprises a third array of at least one unbroken line disposed at an opposite side of the second array from the first array, said third array being parallel with the first array.

4. A stereotactical instrument as claimed in claim 1, wherein said lines of said first and second arrays are made of copper wire arranged on a radiolucent support.

5. A stereotactical instrument as claimed in claim 1, wherein said lines of said first and second arrays are made of tubes which are filled with a substance, for at least one of PET and MRI diagnostics.

6. A stereotactical instrument as claimed in claim 4 wherein the orienting means is releasably attached to the frame.

7. A stereotactical instrument as claimed in claim 3, wherein said lines of said first, second, and third arrays are made of copper wire arranged on a radiolucent support.

8. A stereotactical instrument as claimed in claim 3, wherein said lines of said first, second, and third arrays are made of tubes which are filled with a substance, for at least one of PET and MRI diagnostics.

9. A stereotactical instrument claimed in claim 3, wherein the orienting means is releaseably attached to the frame.

10. A stereotactical instrument as claimed in claim 1, wherein the treatment is radiation treatment.

11. A stereotactical instrument as claimed in claim 1, wherein the position of the area has been previously determined by one of angiogram, PET, DSA, CT, MRI, and X-ray equipment.

12. A stereotactical instrument as claimed in claim 1, wherein the frame is arranged to support an indicating device.

* * * * *